United States Patent [19]

Paterson et al.

[11] Patent Number: 4,681,849

[45] Date of Patent: Jul. 21, 1987

[54] SUNFLOWER INDUCTION, MAINTENANCE AND REGENERATION MEDIA, METHODS OF USE AND PLANTS REGENERATED THEREFROM

[75] Inventors: Karol E. Paterson, Oakland; Nicholas P. Everett, El Sobrante, both of Calif.

[73] Assignee: Stauffer Chemical Company, Richmond, Calif.

[21] Appl. No.: 697,819

[22] Filed: Feb. 4, 1985

[51] Int. Cl.$^4$ ............................ C12N 5/00; C12N 5/02
[52] U.S. Cl. ...................................... 435/240; 435/241
[58] Field of Search ...................... 435/240, 241; 800/1

[56] References Cited

U.S. PATENT DOCUMENTS 4,552,844  11/1985  Everett ................................ 435/240

FOREIGN PATENT DOCUMENTS 0132360  1/1985  European Pat. Off. ............ 435/240

OTHER PUBLICATIONS

Georgieva-Todordva et al, 1980 Proc. 9th Int'l Sunflower Conference, Torremolinos, Spain.
Dodds et al (1982), *Experiments in Plant Tissue Culture*, Cambridge Univ. Press, pp. 27-28.
Paterson, 1984, "Shoot Tip Culture of *Helianthus annus*-Flowering and Development of Adventitious and Multiple Roots", *Am. J. Bot.* v71, pp. 925-931.
Dodds et al, 1982, *Experiments in Plant Tissue Culture*, Cambridge Univ. Press, pp. 25, 101.

*Primary Examiner*—Thomas G. Wiseman
*Assistant Examiner*—David T. Fox
*Attorney, Agent, or Firm*—Michael J. Bradley; Jacqueline S. Larson

[57] ABSTRACT

Sunflower induction, maintenance and regeneration media comprising minimal salts, a carbohydrate source, and regeneration-effective mixtures of plant hormones and regeneration-effective mixtures of vitamins are disclosed and claimed. A method of selecting sunflower seedlines for regeneration using the medium is also disclosed. A method for regenerating sunflower plants using the medium is also disclosed and claimed.

6 Claims, No Drawings

SUNFLOWER INDUCTION, MAINTENANCE AND REGENERATION MEDIA, METHODS OF USE AND PLANTS REGENERATED THEREFROM

FIELD OF THE INVENTION

The instant invention concerns the regeneration of sunflower plants from cultured sunflower tissue. In particular, the invention concerns media for selecting sunflower seed lines that can regenerate sunflower plants from sunflower callus or cell suspensions. Furthermore, the invention relates to a two-step method for regenerating sunflower plants from sunflower callus or cell suspensions.

BACKGROUND OF THE INVENTION

Vegetative propagation of agriculturally important plant species is a well known and valuable practice in some fields of agriculture. In the horticultural arts for example, ornamental flowers are vegetatively propagated from callus. Callus may be defined as a collection of plant cells that have become dedifferentiated usually under the influence of plant hormones such as auxins, for example indole acetic acid (IAA) and auxin-like compounds, for example 2,4-dichloro phenoxyacetic acid (2,4-D). Cellular division of such dedifferentiated plant cells usually produces poorly organized cells that may be further propagated in a growth medium, provided that an auxin or auxin-like plant hormone is present in the growth medium. By adjusting nutrient, vitamin, and plant hormones levels, plants that are essentially identical to the individual plant from which the callus was initiated can be regenerated. For example, using these general methods, the production of thousands of identical orchids is routinely possible from the somatic cells of a single orchid plant.

Vegetative propagation of crop plants by inducing callus, maintaining the callus and regenerating plants from the callus has great potential in the development and improvement of food crops. For example, vegetative propagation may be used to multiply inbred or hybrid plant strains that have commercially valuable or scientifically interesting characteristics which occur rarely or are unstable when the plant reproduces sexually. Tissue obtained from such scientifically interesting or commercially valuable plants can be used to propagate numerous copies of the original plant, thereby stably maintaining the otherwise unstable characteristics.

Callus induced from the tissue of a unique or valuable plant can be multiplied and plants can be regenerated from the callus. Thus multiple copies of a single unique or valuable plant can be reproduced for further breeding, genetic selection or genetic manipulation using recombinant nucleic acid techniques. Plants having unique traits can thus be used in breeding programs without risk of losing the desirable characteristics that may be unstable.

Sunflower (*Helianthus annuus*, hereinafter referred to as *H. annuus*), is one of four major crops grown for edible oil. Ninety percent of the sunflower crop grown in the United States is used for oil production. Development of a system that permits oil-producing inbreds of *H. annuus* to regenerate plants from tissue or callus or suspension culture would be useful as a supplement to current plant breeding programs.

Most reports on tissue culture of *H. annuus* have concerned crown gall cells, i.e., plant tumor cells produced as a result of infection by the bacterial plant pathogen *Agarobacterium tumafaciens*, but there has been some work on callus production from normal sunflower tissues (see for example, Kandler, O., *Planta*, Bd. 40: 346-349 (1952); Henderson et al., *Amer. J. Bot.* 39: 467-473 (1955); Rogers et al., *In Vitro* 9: 462-467 (1974). In addition, there have been three reports of plant or shoot regeneration from cultured sunflower tissue. M. K. Sadhu reported plant regeneration from sunflower stem pith cultured on a modified White's medium with 1 part per million (ppm) indole-acetic acid (IAA) (see Sadhu, M. K., *Indian J. Exp. Biol.*, 12: 110-111 (1979)). Binding et al. reported shoot regeneration from protoplasts isolated from cultured shoot tips, although no details were presented (Binding et al. *Z Planzenphysiol-Bd.* 101: 119-130 (1981)). In these two reports, no information was presented regarding the seed source. The source could have been confectionary (nonoil-producing) hybrids or open pollinated varieties.

A recent report (Guco et al., 1984), also using asynthetic variety, shows regeneration using 2,4-D and BA. No mention is made of the ability to maintain this callus. Georgieva-Todorova et al. reported callus induction and shoot generation from two sterile hybrids—*H. annuus* × *H. decapetalus* and *H. annuus* × *H. hirsutus* (Georgieva-Todordva, et al. *Proc. 9th Int'l Sunflower Conf.* Torremolinos Spain (1980)).

Georgieva-Todorova et al. specifically disclose a medium that allow sunflower callus growth and organogenic regeneration of sunflower shoots from tissue of sterile hybrid sunflower plants. The medium disclosed by Georgieva-Todorova (GT medium) is composed of a range of plant hormones, White's vitamins, and major and minor salts disclosed in Murashige, T. and Skoog, F., (1962) *Physiologia Plantarium*, 15: 443-97. The vitamins disclosed in GT medium are as follows:

| Vitamin Component | Concentration (per 1 medium) |
|---|---|
| thiamine.HCl | 0.1 mg |
| nicotinic acid | 0.5 mg |
| pyridoxine.HCl | 0.5 mg |
| Ca—pantothenate | 1.0 mg |
| inositol | 500.0 mg |
| glycine | 3.0 mg |
| adenine sulfate | 40.0 mg |
| cysteine | 1.0 mg |

The plant hormones disclosed by Georgieva-Todorova et al. are numerous and depending upon the particular mix of hormones and concentration of the particular hormone used in the mix various results are obtained. Thus quick growth of callus with rapid differentiation of meritematic centers is observed in the GT media described above having 0.1 or 10 mg/l benzylamino purine (benzyladenine hereinafter referred to as BA); 0.1 or 10 mg/l indolbutyric acid (hereinafter IBA); 0.1 mg/l BA with 0.1 or 10 mg/l naphthalene acetic acid (NAA); and a combination of 10.0 mg/l BA with 0.1 or 10 mg/l NAA.

Specifically, the best organogenesis was observed in GT medium composed of MS salts and vitamins as described above and the plant hormones as follows: 0.1-0.5 mg/l NAA, 0.1 mg/l BA, and 0.01 mg/l gibberellic acid (GA). The best organogenesis occurred with this mix of plant hormones when the NAA concentration was 0.1 mg/l.

The experiments of Georgieva-Todovova et al. disclose several plant hormone concentrations that appear to permit significant regeneration of sunflower tissue in two sterile hybrid sunflower seed lines. As will be seen below Georgieva-Todorova et al. do not, however, disclose media that may be used to regenerate sunflower tissue from inbred sunflower seed lines. The value of the regeneration medium disclosed by Georgieva-Todovova et al. is thus limited, since the sunflower seed lines to which it has been successfully applied are sterile hybrid seed lines that cannot be used for breeding or genetic selection purposes.

One of the problems facing workers seeking to regenerate sunflower plants from inbred sunflower lines is to develop artificial culture media for callus culture and/or suspension culture (i.e., cells or small clumps of cells suspended in liquid artificial medium) of inbred sunflower lines. A further problem is to identify those inbred sunflower lines that have the potential for successful regeneration of whole plants from callus or suspension culture. The potential of any particular sunflower line to regenerate whole plants is determined by the interaction of the inherent regeneration characteristics of the sunflower line and the medium on which the regeneration of the plants is carried out. Once this regeneration potential has been identified on a sunflower line, it is desirable to develop a media optimized for stably maintaining callus with regeneration potential and for regeneration of sunflower from tissue culture.

As a practical matter, when regenerating from callus or suspensions of sunflower lines identified for their regeneration potential, it is desirable to have a method that can maintain the sunflower callus or suspensions in a condition that permits rapid and prolific regeneration when desired or convenient, yet does not commit the whole sunflower callus or suspensions sample to regeneration and consequent loss of the callus or suspensions line. Media currently used to maintain sunflower callus or suspensions in culture for extended periods of time do not permit any significant regeneration when sunflower callus or suspensions are cultured on them. However, sunflower tissue grown on such maintenance medium for extended periods generally loses the ability to regenerate because, it is believed, the known maintenance media select against regenerable cells and tissues in the callus.

Regeneration media such as that disclosed in Georgievna-Todorova et al. mentioned hereinabove and in the inventors co-pending application Ser. No. 584,079, are effective for inducing regeneration in primary explants from sunflower seedlings and thus are suitable for screening for regeneration potential. These regeneration media, however, are not suitable for maintaining regenerable sunflower callus.

In light of the limitations of conventional maintenance and regeneration media currently in use, it is desirable to develop a medium, hereinafter referred to as induction medium that will stably maintain sunflower callus or suspensions for extended periods of time, at least several months, in a readily regenerable state without causing significant sunflower regeneration. It is furthermore highly desirable to develop a medium, hereinafter referred to as rapid regeneration media, that sustains rapid proliferation and sunflower regeneration, of tissue transferred from the induction medium to the rapid proliferation medium.

OBJECTS AND SUMMARY OF THE INVENTION

One of the objects of the invention is to provide a two-step system for obtaining regenerated sunflowers from sunflower tissue cultured cells including callus or suspensions. Another object of the invention is to provide within this two-step system a method for maintaining readily regenerable sunflower callus or suspensions. A further object of the invention is to provide within this two-step system a method for rapidly regenerating sunflower from the maintained sunflower callus or suspensions. A still further object of the invention is to provide a method of regenerating sunflower in which the callus or suspension from which regeneration occurs may be maintained in a readily regenerable state. Yet another object of the invention is to provide a medium suitable for inducing regenerable sunflower callus or suspension and maintaining it in a readily regenerable state. Yet a further object of the invention is to provide a rapid regeneration medium that sustains rapid proflliferation and regeneration of sunflower tissue. A yet still further object of the invention is to provide sunflower seed plants regenerated by a two-step method in which a sunflower callus or suspensions is induced to a readily regenerable state on a regeneration induction medium and thereafter is regenerated on a rapid differentiation medium. These and other objects of the invention will become readily apparent to those skilled in the art from the following detailed description of the invention which is intended by the inventor to be merely exemplary and is not intended to be limiting.

DETAILED DESCRIPTION OF THE INVENTION

The media according to the instant invention when used together are suitable for regenerating sunflower plants from sunflower callus or suspensions.

"Regeneration" as used herein may be defined as the formation of shoots (organogenic regeneration) or plant embryos (embryogenic regeneration) from somatic cells and the formation of an active plant from the shoots or plant embryo. Regeneration encompasses a number of stages of development. The first stage of embryogenic regeneration is the formation on the callus of small meristemic centers which resemble globular and heart-shaped embryos after two weeks of dark culture on the medium. In the second stage of embryogenic regeneration, these globular and heart-shaped embryos develop into small dark green spots after approximately one week of culture in daylight. These dark green spots on microscopic examination reveal torpedo shaped plant embryos having a shoot and root apex surrounded by an epidermal layer. As described further hereinbelow, these green spots may be further manipulated to produce whole sunflower plants.

According to the invention, the sunflower regeneration media comprises a first medium and a second medium. The first medium is a sunflower regenerable callus induction medium comprised of a minimal salts medium suitable for the growth of plant tissue vitamins suitable for induction of regeneration of sunflower callus, a carbohydrate source such as sucrose and an auxin or synthetic auxin plant hormone either alone or in combination with a gibberellin. In practice, 2,4-diphenoxy acetic acid (2,4-D) and gibberellic acid (GA) are preferred. Vitamins suitable for the induction of regeneration of sunflower callus according to the invention include inositol, thiamine.HCl, nicotinic acid, pyridoxine.HCl, glycine, adenine sulfate, and casamino acids. In practice, it is possible to omit one or another of the above-listed vitamins but the best results are achieved if all the above-listed vitamins are included.

Examples of minimal medium suitable for the growth of plant tissue include B5 medium (Gamborg, O. L., et al., "Nutrient Requirements of Suspension Cultures of Soybean Root Cells," *Expt'l. Cell. Res.,* 50: 151-158 (1968)); MS medium (Murashige, T. and Skoog, F (1962), *Physiologia Plantarium.,* 15: 443-97); N6 medium (Chu, C. et al., "Establishment of an Efficient Medium for Anther Culture of Rice Through Comparative Experiments on the Nitrogen Sources," *Scientia Sinica,* 18: 659-668 (1975); and White's medium (White, P. R., 1963, The Cultivation of Animal and Plant Cells, 2nd ed., Ronald Press, New York, N.Y.).

The following minimal salts are typically found in MS minimal media:

magnesium sulfate.septahydrate ($MgSO_4.7H_2O$),
calcium chloride.dihydrate ($CaCl_2.2H_2O$),
potassium nitrate ($KNO_3$),
ammonium nitrate ($NH_4NO_3$),
potassium phosphate ($KH_2PO_4$),
manganese sulfate.quatrahydrate ($MnSO_4.4H_2O$),
zinc sulfate.septahydrate ($ZnSO_4.7H_2O$),
cupric sulfate.pentahydrate ($CuSO_4.5H_2O$),
cobalt chloride.hexahydrate ($CoCl_2.6H_2O$
potassium iodide (KI),
boric acid ($H_3BO_3$),
sodium molybdinum oxide.dihydrate ($Na_2MoO_4.2H_2O$),
ferrous sulfate.septahydrate ($FeSO_4.7H_2O$), and
sodium ethylenediaminotetracetic acid ($Na_2EDTA$).

In general, as used in the invention, the exact concentration of the salts can be varied within limits without departing from the invention. To standardize the making of the media, however, the concentrations of the above listed minimal salts are as follows:

| | |
|---|---|
| $MgSO_4.7H_2O$ | 370 milligrams/liter (mg/l) |
| $CaCl_2.2H_2O$ | 440 mg/l |
| $KNO_3$ | 1900 mg/l |
| $NH_4NO_3$ | 1650 mg/l |
| $KH_2PO_4$ | 170 mg/l |
| $MnSO_4.4H_2O$ | 22.3 mg/l |
| $ZnSO_4.7H_2O$ | 8.6 mg/l |
| $CuSO_4.5H_2O$ | 0.025 mg/l |
| $CoCl_2.6H_2O$ | 0.025 mg/l |
| KI | 0.83 mg/l |
| $H_3BO_3$ | 6.2 mg/l |
| $Na_2MoO_4.2H_2O$ | 0.25 mg/l |
| $FeSO_4.7H_2O$ | 28.75 mg/l |
| $Na_2EDTA$ | 37.25 mg/l |

The plant hormones in the first medium have been found to effectively induce regenerable callus when used in the range of 0.05 to 0.5 mg/l 2,4-D with an optimum of 0.1 mg/l 2,4-D. It is preferred that the first medium contain in addition to 2,4-D an amount of GA. The effective GA concentration range is between 0.005 to 0.5 mg/l with an optimum of 0.1 mg/l GA. The preferred first medium thus comprises a minimal salts plant growth medium such as MS medium, vitamins including inositol, thiamine HCl, nicotinic acid, pyridoxine.HCl, glycine, adenine sulfuate, 0.1 mg/l 2,4-D and 0.1 mg/l GA.

The first medium is used for inducing regenerable sunflower callus in a sunflower tissue culture in a two-step method that is described further hereinbelow.

The second medium according to the invention is a sunflower regeneration differentiation medium comprised of a minimal salts medium suitable for the growth of plant tissue as described hereinabove, vitamins, a carbohydrate source such as sugar, a cytokinin such as a benzyladenine (BA) either alone or in combination with gibberellic acid. Vitamins suitable for the regeneration differentiation of sunflower callus according to the invention include those vitamins listed hereinabove for the first medium. In practice, it is possible to omit one or another of the above-listed vitamins but the best results are achieved if all of the above listed vitamins are included.

The concentration of BA in the second medium is in a range between 0.05 and 2 mg/l. Best results are obtained when the BA concentration is between 0.1 and 1.0 mg/l with a preferred concentration of 1 mg/l BA.

The concentration of gibberellic acid in the second medium is in a range of 0.005 and 0.5 mg/l. The best results are obtained in a range of from 0.01 to 0.1 mg/l GA with the preferred concentration of 0.1 mg/l.

The uses of the medium according to the invention include the induction and maintenance of regenerable callus tissue and the regeneration of sunflower plants from sunflower tissue in culture. The invention thus includes a method of regenerating sunflower plants from sunflower callus tissue comprising: providing a callus of sunflower tissue, growing the tissue on a sunflower regeneration induction medium according to the invention transferring the induced sunflower callus to rapid regeneration differentiation medium and growing the induced callus thereon until green spots form on the callus and shoots form from the green spots.

The shoots so formed may be grafted onto sunflower seedlings using grafting techniques as described in Haberman H. H. and R. H. Wallace, *Amer. J. Bot.,* 45: 479-482 (1958). Alternatively, the callus having shoots may be transferred to a root-forming medium and grown thereon until roots form. Such root forming media are generally growth media such as MS medium or White's medium or other growth medium without hormones or with a cytokinin such as BA.

It is also preferable to use callus derived from hypocotyl segments of sunflower plants to be regenerated. The hypocotyl segments are taken from seedlings 3-21 days old, preferably more than 10 days old. The hypocotyl segments are grown for a period of time in complete darkness, on the regeneration induction medium and are transferred to the rapid regeneration medium for a period of daily dark and light. Preferably, the hypocotyl segments are grown on the regeneration medium in complete darkness for 1-4 weeks, preferably 4 weeks, followed by about 1-2 weeks of 16 hours per day at 1000 to 3000 lux, 8 hours dark on rapid regeneration differentiation medium.

After transfer of the callus from regeneration induction medium to regeneration differentiation medium and the formation of green spots, the callus remains on the regeneration differentiation medium for a period of time sufficient to form shoots from the green spots, generally 2-4 weeks. Once the shoots have formed the callus may be removed to an appropriate rooting medium, which is preferably hormone-free. Plants having roots may be planted in soil to grow out, rootless shoots may be grafted to greenhouse grown seedlings according to well known procedures. (See, e.g., Habermann et al. supra.)

The regeneration of a sunflower plant from tissue in culture is the result of the genotype of the sunflower plant, i.e., its inherent capacity for regeneration, and the conditions under which the sunflower plant is grown, i.e., the adequacy of the medium or media used to sustain regeneration of the sunflower plant. Using the media described above it is possible to regenerate sunflower lines by the methods described in the following examples. The following examples are intended by the inventor to be merely descriptive and non-limiting examples of the media an uses thereof.

EXAMPLE 1

*Helianthus annuus* inbred line SS415B was grown aseptically. For aseptic growth the seeds were sterilized in 40% chlorine bleach with several drops of detergent for 20 minutes and rinsed with sterile water. The seed were germinated in tubes of agar media made of B5 salts (Gamborg, O. L. et al., "Nutrient Requirements of Suspension Cultures of Soybean Root Cells," *Experimental Cell Research*, 50: 148-151, 1968), 0.5% sucrose, 0.1 mg/l thiamine, 0.5 mg/l nicotinic acid, 0.5 mg/l pyridoxine.HCl, 100 mg/l inositol, 500 mg/l casamino acids, 40 mg/l adenine sulfate and 0.8% agar. Explants sources were 2-3 mm hypocotyl segments from 11 day old seedlings.

A sunflower regeneration induction medium was prepared containing minimal salts as listed below. In the following examples each component is listed at its final concentration in the medium.

| | |
|---|---|
| $MgSO_4.7H_2O$ | 370 milligrams/liter (mg/l) |
| $CaCl_2.2H_2O$ | 440 mg/l |
| $KNO_3$ | 1900 mg/l |
| $NH_4NO_3$ | 1650 mg/l |
| $KH_2PO_4$ | 170 mg/l |
| $MnSO_4.4H_2O$ | 22.3 mg/l |
| $ZnSO_4.7H_2O$ | 8.6 mg/l |
| $CuSO_4.5H_2O$ | 0.025 mg/l |
| $CoCl_2.6H_2O$ | 0.025 mg/l |
| KI | 0.83 mg/l |
| $H_3BO_3$ | 6.2 mg/l |
| $Na_2MoO_4.2H_2O$ | 0.25 mg/l |
| $FeSO_4.7H_2O$ | 28.75 mg/l |
| $Na_2EDTA$ | 37.25 mg/l |

The minimal salts were supplemented with vitamins as follows:

100 mg/l inositol
0.5 mg/l nicotinic acid
0.5 mg/l pyridoxine.HCl
1.0 mg/l thiamine
2 mg/l glycine
40 mg/l adenine sulfate 500 mg/l casamino acids were added.

A synthetic plant hormone 2,4-D was added to the regeneration induction medium at a concentration of 0.1 mg/l. A second regeneration induction medium including the above and gibberellic acid to a concentration of 0.1 mg/l was prepared.

Four 11 day old 2-3 mm hypocotyl segments were placed on the two media for two weeks in complete darkness during which time callus tissue proliferated. The segments and callus were transferred to a regeneration differentiation medium for differentiation amd were grown thereon for one week in the light at 1000 to 3000 lux for 16 hr. light/8 hr. dark per day (DL). The regeneration differentiation media had the same components as the induction medium except that the hormone concentrations were as listed in the left column of Table 1. Regeneration frequency, was scored as the number of the number of green spots developing on callus per hypocotyl segment and is indicated in Table 1.

TABLE 1

| Sunflower Regeneration - Green spots/Plate Induction Medium (2 weeks dark) | | |
|---|---|---|
| Regeneration Medium 1 wk DL with mg/l | 0.1 mg/ 2,4-D | 0.1 mg/2,4-D and 0.1 mg/l GA |
| no hormones | 0.4 ± 0.3 | 0.7 ± 0.4 |
| 0.01 GA | 0.9 ± 0.3 | 0.6 ± 0.2 |
| 0.1 GA | 0.4 ± 0.2 | 0.3 ± 0.2 |
| 1.0 BA | 1.0 ± 0.4 | 1.6 ± 0.4 |
| 0.1 BA | 3.1 ± 0.4 | 3.0 ± 0.6 |
| 0.1 BA, 0.01 GA | 0.5 ± 0.2 | 2.1 ± 0.5 |
| 1.0 BA, 0.1 GA | 1.1 ± 0.4 | 2.6 ± 0.3 |
| 1.0 NAA, 0.1 BA 0.01 GA | 0.9 ± 0.3 | 0.9 ± 0.3 |
| 1.0 NAA, 1.0 BA 0.1 GA | 0.9 ± 0.3 | 2.5 ± 0.4 |
| 0.1 2,4-d | 0.1 ± 0.1 | — |
| 0.1 2,4-D, 0.01 GA | — | 0.1 ± 0.1 |

The results indicate that the sunflower regeneration differentiation medium with plant hormone concentrations of 0.1 mg/l BA and 0.1 mg/l GA produced the greatest amount of regeneration. The same medium with 0.1 mg/l BA also induced regenerable callus but with lower frequency in most cases using this inbred sunflower line.

The results also indicate that the presence of benzyladenine (BA) in the differentiation medium at a concentration of at least 0.1 mg/l and preferably about 1.0 mg/l enhances regeneration. Furthermore, the addition of GA to the differentiation medium in an amount of 0.01 mg/l appears to sustain the formation of green spots when the hypocotyl segments are induced with gibberellic acid-containing induction medium.

EXAMPLE 2

Hypocotyl segments were obtained as in Example 1 above and were placed on regeneration induction media having the same composition as in Example 1 except that the plant hormone concentrations were varied as shown in Table 2. The hypocotyl segments were cultivated for 13 weeks in the dark on the regeneration induction media and were transferred during this period every 2 weeks to fresh regeneration induction medium. At the end of 13 weeks approximately equal volumes of each callus were placed into 25 ml liquid MS medium containing 1.0 mg/l benzyladenine and 10% coconut water in flasks and were agitated in a rotary shaker at 130 rpm for 1 hour to form cell suspensions. Three ml aliquots were pipetted from the cell suspensions to covered petri plates of the regeneration differentiation medium of Example 1 except that one set of plates had plant hormone concentrations of 1 mg/l NAA, 1 mg/l benzyladenine, 0.1 mg/l gibberellic acid and the other set of plates had 1.0 mg benzyladenine. Both sets of plates also contained 10% coconut water. The results for inbred 415B and 410B are shown in Tables 2-A and 2-B, respectively, as green spots per plate.

TABLE 2-A

Sunflower Regeneration in Green spots per Plate

| Induction Medium 13 Weeks Dark | Differentiation Medium (2 Weeks Light) 1.0 mg/l NAA, 1.0 mg/l BA, 1.0 mg/l GA | 1 mg/l BA |
|---|---|---|
| 0.1 mg/l 2,4-D | 8.3 ± 3.2 | 1.7 ± 2.2 |
| 0. mg/l 2,4-D + 1.0 mg/l NAA | 10.3 ± 6.6 | 0.7 ± 0.8 |
| 0.1 mg/l 2,4-D + 0.1 mg/l GA | 27.7 ± 8.9 | 8.0 ± 3.7 |
| 0.1 mg/l 2,4-D 0.01 mg/l GA 1.0 mg/l NAA | 23.7 ± 6.6 | 4.0 ± 1.2 |

TABLE 2-B

Sunflower Regeneration in Green spots per Plate

| Induction Medium 13 Weeks Dark | Differentiation Medium (2 Weeks Light) 1.0 mg/l NAA, 1.0 mg/l BA, 1.0 mg/l GA | 1 mg/l BA |
|---|---|---|
| 0.1 mg/l 2,4-D | 2.0 ± 1.9 | 0 |
| 0. mg/l 2,4-D + 1.0 mg/l NAA | 4.3 ± 2.7 | 0 |
| 0.1 mg/l 2,4-D + 0.1 mg/l GA | 10.3 ± 4.8 | 1.3 ± 1.1 |
| 0.1 mg/l 2,4-D 0.01 mg/l GA 1.0 mg/l NAA | 9.3 ± 3.5 | 1.7 ± 2.1 |

The results clearly indicate that the addition of gibberellic acid to the induction medium markedly increases regeneration. It also indicates that the presence or absence of NAA in the induction medium does not significantly affect regeneration.

The results also confirm that the addition of GA to the differentiation medium substantially improves the rate of regeneration as compared to regeneration medium having BA but no GA.

EXAMPLE 3

Eight-day-old hypocotyl segments were obtained as in Example 1 hereinabove and were placed on regeneration induction medium having the same minimal salts, carbon source, vitamins and amino acids as in Example 1. The regeneration induction media were supplemented with either 0.1 mg/l 2,4-D and 1 mg/l NAA or 0.1 mg/l 2,4-D, 1 mg/l NAA, 1 mg/l BA and 0.1 mg/l GA.

After 2 weeks growth in complete darkness on the regeneration induction media the hypocotyl segment and any callus that had grown were either transferred to regeneration differentiation media for growth under light conditions for eight days or were not transferred but grown under light conditions for 8 days on regeneration differentiation medium. The regeneration differentiation media had the hormone concentrations listed in Table 3.

TABLE 3

Regeneration in Green spots per Segment

| Regeneration Medium | Induction Medium - Hormones (mg/l) | |
|---|---|---|
| | 1.0 NAA, 1.0 BA, 0.1 GA, 0.1 2,4-D | 1.0 NAA, 0.1 2,4-D |
| untransferred | 1.9 ± 0.4 | 0.1 ± 0.4 |
| 1.0 NAA, 1.0 BA, 0.1 GA | 1.7 ± 0.3 | 0.3 ± 0.1 |
| 0.1 2,4-D | 1.6 ± 0.4 | 0.03 ± 0.03 |
| 1.0 BA, 0.1 GA | 3.2 ± 0.5 | 0.8 ± 0.2 |
| Ha medium, 1.0 NAA, 1.0 BA | 1.7 ± 0.4 | 0.2 ± 0.1 |

The results indicate that both NAA and 2,4-D in the regeneration differentiation medium tends to decrease the frequency of sunflower regeneration as compared to regeneration medium containing BA and GA. The results clearly indicate that the best regeneration media contains both BA and GA.

EXAMPLE 4

Hypocotyl segments were obtained from 12 day old seedlings as in Example I, and were placed on regeneration induction medium having 0.1 mg/l 2,4-D. The hypocotyl segments were grown on the medium for 3, 7, 11 or 14 days prior to transfer into regeneration differentiation medium. The regeneration differentiation medium contained the hormones listed in Table IV below. Tissues were covered for regeneration 3 weeks after initiation on the regeneration induction medium.

TABLE 4

| Induction Medium 0. mg/l, 2,4-D | Regeneration Medium | | | |
|---|---|---|---|---|
| | 1.0 mg/l NAA 1.0 mg/l BA 0.1 mg/l GA | 1.0 mg/l BA 0.1 mg/l GA | 1.0 mg/l BA | 0.1 mg/l 2,4-D |
| 3 days | 0.6 ± 0.3 | 0.3 ± 0.2 | 1.1 ± 0.4 | 0 |
| 7 days | 3.5 ± 0.5 | 4.1 ± 0.4 | 1.0 ± 0.3 | 0 |
| 11 days | 1.0 ± 0.4 | 1.9 ± 0.3 | 0 | 0 |
| 14 days | 0.4 ± 0.2 | 0.2 ± 0.1 | 0 | 0 |

The results indicate that at least 7 days are required on induction medium to achieve the best frequency of regeneration on this induction media.

The tissues were left on the regeneration differentiation media, shoots formed from green spots only on the regeneration medium containing GA and BA but no NAA.

EXAMPLE 5

The hormones in callus induction media and the regeneration media were varied along with the time for callus induction and regeneration. Three callus induction media were tested—0.1 mg/l 2,4-D (HaRD); 0.1 mg/l 2,4-D+0.1 mg/l GA (HaRDG); and 0.1 mg/l 2,4-D+1 mg/l BA+)0.1 mg/l Ga (HaRDBG). After induction of callus on these media in the dark, the callus was transferred to 4 regeneration media—HaRD (0.1 mg/l 2,4-D); HaB 1 mg/l BA); HaG (0.1 mg/l GA); or HaBG (1 mg/l BA+0.1 mg/l GA). The amount of regeneration (green spots/callus piece) was counted after 1, 2 or 4 weeks in the light. The results are shown in Tables 5-A through 5-C.

When the callus induction period was only 1 week (Table 5-A), the amount of regeneration was generally low. As the callus induction time increased (Table 5-D and 5-C), the amount of regeneration, in general, increased. This was especially true when the callus induction media was HaRDG. HaRDG appeared to be the best callus induction medium. The best callus induction time was 4 weeks and the best regeneration time was 2 weeks.

The best regeneration media when green spots per piece were counted was HaB (Table 5-C). Unfortunately when left on this media many of these green spots did not develop into shoots, but recallused (see week 4 of Table 5-C). When regeneration was measured after 4 weeks in the light as the number shoots per callus piece (Table 5-C), then the best regeneration media was HaBG.

Under the best conditions (4 weeks in the dark on HaRDG followed by light culture on HaBG) 70% of the green spots developed into shoots.

| Definition for Tables 5-A, 5-B, 5-C and 5-D (mg/l hormones) | |
|---|---|
| HaRD | 0.1 2,4-D |
| HaRDG | 0.1 2,4-D + 0.1 GA |
| HaRDBG | 0.1 2,4-D + 1.0 BA + 0.1 GA |
| HaB | 1.0 BA |
| HaG | 0.1 GA |
| HaBG | 1.0 BA + 0.1 GA |

TABLE 5-A

The Amount of Regeneration (Green spots/plate) From 1 Week Old, Dark-grown Hypocotyl-Derived Callus after 1, 2 and 4 weeks in the light. (* = most)

| Callus Media | Regeneration Media | Weeks in the light | | |
|---|---|---|---|---|
| | | 1 | 2 | 4 |
| HaRD | HaRD | 0 | 0.1 ± 0.1 | 0.4 ± 0.2 |
| | HaB | 0.2 ± 0.1 | 0.3 ± 0.2 | 0 |
| | HaG | 0.3 ± 0.1 | 0.1 ± 0.1 | 0 |
| | HaBG | 0.1 ± 0.1 | 0.2 ± 0.1 | 0 |
| HaRDG | HaRD | 0 | 0.1 ± 0.1 | 0.7 ± 0.2 |
| | HaB | 0.2 ± 0.1 | 0.6 ± 0.2 | 0.3 ± 0.1 |
| | HaG | 0 | 2.0 ± 0.7* | 0 |
| | HaBG | 0.2 ± 0.1 | 0.7 ± 0.4 | 0 |
| HaRDBG | HaRD | 0 | 0 | 0 |
| | HaB | 0.2 ± 0.1 | 1.3 ± 0.9 | 0.1 ± 0.1 |
| | HaBG | 0 | 0.1 ± 0.1 | 0 |
| | HaBG | 0 | 0.2 ± 0.1 | 0.1 ± 0.1 |

TABLE 5-B

The amount of regeneration (green spots/plate) from 2 week old, dark-grown, hypocotyl-derived callus after 1, 2 and 4 weeks in the light. (* = most)

| Callus Media | Regeneration Media | Weeks in the light | | |
|---|---|---|---|---|
| | | 1 | 2 | 4 |
| HaRD | HaRD | 0.2 ± 0.2 | 0.5 ± 0.2 | 0.6 ± 0.1 |
| | HaB | 1.0 ± 0.2 | 1.6 ± 0.3 | 0.2 ± 0.1 |
| | HaG | 0.3 ± 0.1 | 1.4 ± 0.3 | 0 |
| | HaBG | 0.5 + 0.2 | 1.7 ± 0.4 | 0 |
| HaRDG | HaRD | 0 | 0.5 ± 0.1 | 1.5 ± 0.4 |
| | HaB | 3.5 ± 0.4 | 4.5 ± 0.5* | 1.6 ± 0.3 |
| | HaG | 0.5 ± 0.1 | 3.6 ± 0.4* | 0.1 ± 0.1 |
| | HaBG | 2.8 ± 0.4 | 3.9 ± 0.4* | 0.2 ± 0.2 |
| HaRDBG | HaRD | 0.1 ± 0.1 | 0.1 ± 0.1 | 4.2 + 1.1 |
| | HaB | 0.1 ± 0.1 | 0.2 ± 0.1 | 0 |
| | HaBG | 0 | 0.7 ± 0.2 | 0 |
| | HaBG | 0.1 ± 0.1 | 0 | 0 |

TABLE 5-C

The amount of regeneration (green spots/plate) from 4 week old, dark-grown, hypotocyl-derived callus after 1, 2 and 4 weeks in the light. (* — most)

| Callus Media | Regeneration Media | Weeks in the light | | |
|---|---|---|---|---|
| | | 1 | 2 | 4 |
| HaRD | HaRD | 0.2 ± 0.1 | 1.0 ± 0.4 | 0.6 ± 0.2 |
| | HaB | 0.8 ± 0.2 | 2.0 ± 0.4 | 0.7 ± 0.2 |
| | HaG | 0.3 ± 0.2 | 0.9 ± 0.2 | 0.6 ± 0.2 |
| | HaBG | 0.3 ± 0.1 | 1.3 ± 0.3 | 0 |
| HaRDG | HaRD | 0.5 ± 0.2 | 1.0 ± 0.2 | 1.4 ± 0.3 |
| | HaB | 5.7 ± 0.5 | 11.9 ± 0.7* | 3.0 ± 0.4 |
| | HaG | 0.8 ± 0.3 | 2.6 ± 0.4* | 1.0 ± 0.2 |
| | HaBG | 5.0 ± 0.5 | 4.2 ± 0.7 | 1.1 ± 0.3 |
| HaRDBG | HaRD | 0.2 ± 0.1 | 0.2 ± 0.1 | 0.6 ± 0.2 |
| | HaB | 0.3 ± 0.1 | 1.6 ± 0.5 | 0.5 ± 0.2 |
| | HaBG | 0.3 ± 0.2 | 0.7 ± 0.3 | 0.1 ± 0.1 |
| | HaBG | 0 | 0.3 ± 0.1 | 0 |

TABLE 5-D

The number of shoots/plate after 4 weeks in the light. Prior to light culture, callus was grown in the dark for 1, 2 or 4 weeks. (* = most)

| Callus Media | Regeneration Media | Weeks in the light | | |
|---|---|---|---|---|
| | | 1 | 2 | 4 |
| HaRD | HaRD | 0 | 0 | 0 |
| | HaB | 0 | 0.1 ± 0.1 | 0 |
| | HaG | 0 | 0 | 0.1 ± 0.1 |
| | HaBG | 0.1 ± 0.1 | 0 | 0 |
| HaRDG | HaRD | 0 | 0 | 0 |
| | HaB | 0 | 0.1 ± 0.1 | 0.1 ± 0.1 |
| | HaG | 0 | 0.1 ± 0.1 | 0.2 ± 0.1 |
| | HaBG | 0.1 ± 0.1 | 0.7 ± 0.3 | *3.4 ± 1.3 |
| HaRDBG | HaRD | 0 | 0 | 0 |
| | HaB | 0.1 ± 0.1 | 0.1 ± 0.1 | 0 |
| | HaBG | 0 | 0 | 0.1 ± 0.1 |
| | HaBG | 0 | 0.1 ± 0.1 | 0 |

EXAMPLE 6

Nodule, slimy callus from hypocotyls of 410B and 415B has been selected and maintained in the dark for 5–8 months on various media.

One batch of 415B callus was maintained on HaRDGB media (2,4-D, BA, GA) where the 2,4-D concentration was either 0.1 or 0.5 mg/l. The callus grew faster and required less selection (i.e., removal of nonnodular callus) on the higher 2,4-D concentration. When tested for regeneration, he variation was great, but the results suggested that increasing the 2,4-D concentration may decrease regeneration (Table 6-A).

To test the effect of no cytokinin on regeneration nodular callus from 410B and 415B was maintained for 25 weeks on 2,4-D (HaRD)±NAA or 2,4-D and GA (HaRDG)±NAA. Four regeneration media were also tested (Tables 6-B and 6-C). With both inbreds there was more regeneration from callus that had been maintained with both 2,D-D and GA. 410B callus maintained with NAA regenerated better while 415B callus regenerated best with or without NAA in the maintenance media. 415B callus regenerated best on HaR media with or without coconut water. Although 410B regenerated the most on HaR+coconut water, there was no significant difference between that and HaBG-+coconut water.

TABLE 6-A

Regeneration (green spots/plate) from 32-week old, dark-grown 415B callus maintained on HaRDGB with 0.1 or 0.5 mg/l 2,4-D. All cultures hae 1 mg/l BA + 0.1 mg/l GA. Each plate contained 0.5 gm callus on HaR + 10% (v/v) coconut water.

Maintained on:
Regeneration (gs/plate)

| | 1 week | 2 weeks |
|---|---|---|
| 0.1 2,4-D | 4.0 ± 4.3 | 21.7 ± 20.7 |
| 0.5 2,4-D | 1.6 ± 0.9 | 7.1 ± 2.0 |

TABLE 6-B

Regeneration (green spots/plate) from 25 week old, dark-grown 415B callus. Each treatment consists of 4 plates with 0.6 gm callus/plate. (* = most regeneration.)

Maintenance Media

| Regeneration media | HaRD 1 | HaRD + NAA | HaRDG | HaRDG + NAA |
|---|---|---|---|---|
| HaR | 2.8 ± 1.8 | 9.0 ± 3.8 | 24.8 ± 5.7* | 23.5 ± 2.4* |
| HaR + CW | 3.5 ± 1.8 | 5.0 ± 1.7 | 24.8 ± 5.5* | 23.8 ± 8.2* |
| HaBG | 6.0 ± 1.4 | 10.8 ± 2.1 | 10.8 ± 2.8 | 11.3 ± 1.0 |
| HaBG + CW | 6.3 ± 1.9 | 7.8 ± 1.6 | 6.5 ± 3.2 | 9.5 ± 2.1 | mg/l
HaR = 1 NAA + 1 BA + 0.2 GA
HaBG = 1 BA + 0.1 GA
HaRD = 0.1 2,4-D
HaRDG = 0.1 2,4-D + 0.1 GA
NAA = 1 NAA
CW = 10% (v/v) coconut water

TABLE 6-C

Regeneration (green spots/plate after 2 weeks in the light) from 25 week old, dark-grown 415B callus. Each treatment consists of 4 plates with 0.6 gm callus/plate. (* = most regeneration.)

Maintenance Media

| Regeneration media | HaRD 1 | HaRD + NAA | HaRDG | HaRDG + NAA |
|---|---|---|---|---|
| HaR | 1.5 ± 1.1 | 0.3 ± 0.3 | 2.8 ± 1.6 | 0 |
| HaR + CW | 2.8 ± 1.8 | 3.3 ± 3.4 | 4.3 ± 2.3 | 11.0 ± 5.9* |
| HaBG | 0 | 2.0 ± 1.4 | 2.8 ± 2.2 | 8.5 ± 4.5* |
| HaBG + CW | 0 | 2.8 ± 2.9 | 0.3 ± 0.3 | 6.3 ± 4.7* | mg/l
HaR = 1 NAA + 1 BA + 0.2 GA
HaBG = 1 BA + 0.1 GA
HaRD = 0.1 2,4-D
HaRDG = 0.1 2,4-D + 0.1 GA
NAA = 1 NAA
CW = 10% (v/v) coconut water

EXAMPLE 7

Suspensions cultures of two sunflower inbreds (SS410B and SS415B) were developed from maintainable callus still capable of plant regeneration. To initiate cultures, 8-10 gm of callus were added to 50 ml of the following media:

MA salts and vitamins
0.1 or 0.5 mg/l 2,4-D
0.1 mg/l GA
30 gm/l sucrose
10% (v/v) coconut water
0 or 500 mg/l casamino acids
pH-5.8

Flasks were placed on rotary shakers (130 rpm) under low light (100-800 lux). Suspended cells were transferred once a week by leeting the denser cells settle, pouring off the old media and less dense cells, and adding 50 ml fresh media to the dense cells.

After 32 weeks in suspension the regeneration frequencies of these suspensions were as follows:

| SS410B | 52.8 ± 7.8 plantlets/0.5 gm cells |
|---|---|
| SS415B | 46.1 ± 10.2 plantlets/0.5 gm cells |

What is claimed is:

1. An inbred sunflower tissue cultured cells induction and maintenance effective media and shoot regeneration effective media system comprising:
   (a) an induction and maintenance effective media comprising MS salts, MS vitamins, about 30 g/L sucrose, about 500 mg/L casamino acids or about 500 mg/L casamino acids and about 40 mg/L adenine sulfate, from about 0.05 to about 0.5 mg/L 2,4-dichlorophenoxy acetic acid or from about 0.05 to about 0.5 mg/L 2,4-dichlorophenoxy acetic acid and about 1 mg/L naphthalenic acid, and from about 0.005 mg/L to about 0.4 mg/L gibberellic acid; and
   (b) a shoot regeneration effective media comprising MS salts, MS vitamins, about 30 g/L sucrose, about 500 mg/L casamino acids or about 500 mg/L casamino acids and about 40 mg/L adenine sulfate, from about 0.05 mg/L to about 2 mg/L benzyladenine and from about 0.005 mg/L to about 0.5 mg/L gibberellic acid.

2. The system of claim 1 wherein the 2,4-dichlorophenoxy acetic acid is about 0.1 mg/L, the gibberellic acid is about 0.1 mg/L and the benzyladenine is about 1 mg/L.

3. The system of claim 2 wherein the regeneration effective media additionally contains about 100 g/L coconut water.

4. A method for regenerating inbred sunflower shoots from inbred sunflower tissue cultured cells comprising:
   (a) providing inbred sunflower tissue cultured cells;
   (b) growing the cells on a sunflower tissue cultured cell induction and maintenance effective media comprising MS salts, MS vitamins, about 30 g/L sucrose, about 500 mg/L casamino acids or about 500 mg/L casamino acids and about 40 mg/L adenine sulfate, from about 0.05 to about 0.5 mg/L 2,4-dichlorophenoxy acetic acid or from about 0.05 to about 0.5 mg/L 2,4-dichlorophenoxy acetic acid and about 1 mg/L naphthalenic acid, and from about 0.005 mg/L to about 0.4 mg/L gibberellic acid, to induce growth of additional cells and maintain the cells; and
   (c) growing the resultant cells of step (b) on a sunflower tissue cultured cell regeneration effective media comprising MS salts, MS vitamins, about 30 g/L sucrose, about 500 mg/L casamino acids or about 500 mg/L casamino acidsa and about 40 mg/L adenine sulfate, from about 0.05 mg/L to about 2 mg/L benzyladenine and from about 0.005 mg/L to about 0.5 mg/L gibberellic acid, until shoots form on the culture cells.

5. The method of claim 4 wherein the 2,4-dichlorophenoxy acetic acid is about 0.1 mg/L, the gibberellic acid is about 0.1 mg/L and the benzyladenine is about 1 mg/L.

6. The method of claim 5 wherein the regeneration effective media additionally contains about 100 g/L coconut water.

* * * * *